United States Patent
Wiles et al.

(10) Patent No.: US 6,849,422 B1
(45) Date of Patent: Feb. 1, 2005

(54) SYSTEM AND METHOD FOR ANALYZING ANTIBIOTIC SUSCEPTIBILITY OF BIOLOGICAL SAMPLES USING REDOX AND TURBIDITY MEASURMENTS TO ASCERTAIN MINIMUM INHIBITORY CONCENTRATIONS (MICS)

(75) Inventors: Timothy M. Wiles, Reisterstown, MD (US); David J. Turner, Owings Mills, MD (US); Michael A. O'Connell, Durham, NC (US); Giovanni Parmigiani, Baltimore, MD (US); Merlise Clyde, Durham, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 733 days.

(21) Appl. No.: 09/583,891

(22) Filed: May 31, 2000

(51) Int. Cl.[7] ............................................... C12Q 1/02
(52) U.S. Cl. ............................................................ 435/29
(58) Field of Search ............................................. 435/29

(56) References Cited

U.S. PATENT DOCUMENTS

| | | | | |
|---|---|---|---|---|
| 4,448,534 A | * | 5/1984 | Wertz et al. ................. 356/435 |
| 5,501,959 A | * | 3/1996 | Lancaster et al. ............. 435/32 |
| 5,528,363 A | * | 6/1996 | Fachinger et al. ........... 356/326 |
| 6,096,272 A | * | 8/2000 | Clark et al. ..................... 422/64 |
| 6,251,624 B1 | * | 6/2001 | Matsumura et al. ........... 435/34 |
| 6,372,485 B1 | * | 4/2002 | Clark et al. ................ 435/288.7 |
| 6,395,506 B1 | * | 5/2002 | Pitner et al. .................... 435/32 |
| 6,436,631 B1 | * | 8/2002 | Bochner .......................... 435/4 |

* cited by examiner

*Primary Examiner*—Ralph Gitomer
(74) *Attorney, Agent, or Firm*—Bruce S. Weintraub

(57) ABSTRACT

A system and method for analyzing samples, such as biological samples, to accurately and effectively determine the susceptibility of the samples to antimicrobial materials, so as to determine minimum inhibitory concentration (MIC) values for the respective samples and antimicrobial materials. At each of a plurality of time intervals, the system and method directs a plurality of different analyzing light wavelengths, such as red, green and blue wavelengths, onto each of a plurality of sample wells, and detects a respective resultant light wavelength emanating from the respective sample wells for each of the analyzing light wavelengths. The system and method uses resultant light wavelengths to generate at least two growth indicator characteristic curves representing, for example, the redox state and turbidity characteristics of the sample wells. The system then uses the redox state and turbidity characteristics of sample wells containing the same antimicrobial material to determine the MIC value for that material in relation to the sample contained in those wells.

8 Claims, 11 Drawing Sheets

SYSTEM AND METHOD FOR ANALYZING ANTIBIOTIC SUSCEPTIBILITY OF BIOLOGICAL SAMPLES USING REDOX AND TURBIDITY MEASURMENTS TO ASCERTAIN MINIMUM INHIBITORY CONCENTRATIONS (MICS)

CROSS-REFERENCE TO RELATED APPLICATION

Related subject matter is disclosed in a copending U.S. patent application of Clark et al., entitled "Automated Microbiological Testing Apparatus and Methods Therefor", Ser. No. 09/083,130, filed May 22, 1998, the entire contents of which are incorporated herein by reference.

BACKGROUND OF THE INVENTION

1. Field of the Invention

The present invention relates to a system and method for analyzing samples, such as biological samples, to determine the susceptibility of the samples to antimicrobial materials, such as antibiotics. More particularly, the present invention relates to a system and method which takes a plurality of optical readings of a biological sample contained in sample wells of a sample test panel having various types and concentrations of antimicrobial materials therein and, based on these readings, determines the respective minimum inhibitory concentrations (MICs) at which the respective antimicrobial materials will inhibit growth of the sample.

2. Description of the Related Art

Many conventional systems exist for performing tests on microbiological samples related to patient diagnosis and therapy. The microbiological samples may come from a variety of sources, including infected wounds, genital infections, cerebro-spinal fluids, blood, abscesses or any other suitable source. From the microorganism samples, an inoculum is prepared in accordance with established procedures which produce a bacterial or cellular suspension of a predetermined concentration. Further processing of the suspension may depend on the testing method employed, as can be appreciated by one skilled in the art.

The conventional systems are used, for example, to identify the types of microorganisms present in a patient's sample. Typically, in such systems, reagents are placed into cupules, or test wells, of identification trays, into which the sample is introduced. The reagents change color in the presence of an actively growing culture of microorganisms. Based on the color change, or lack thereof, the microorganism can be identified by the use of reference tables.

Other systems have been developed for susceptibility testing of microorganisms. These systems are used to determine the susceptibility of a microorganism in a sample to various therapeutics, such as antibiotics. Based on these test results, physicians can then, for example, prescribe an antimicrobial product which will be successful in eliminating or inhibiting growth of the microorganism. Qualitative susceptibility testing, in particular, provides an indication of whether a microorganism is resistant or sensitive to a particular antibiotic, but does not provide an indication on the degree of sensitivity or resistance of the microorganism. On the other hand, quantitative susceptibility testing provides an indication of the concentration of the antimicrobial agent needed to inhibit growth of the microorganism. The term minimum inhibitory concentration (MIC) is used to refer to the minimum concentration of the antimicrobial agent that is required to inhibit the growth of a microorganism.

Although the conventional systems can be somewhat useful in determining the MICs at which respective antimicrobial agents will inhibit growth of respective microorganisms, these systems have certain drawbacks. For example, when performing identification and susceptibility testing, the test trays are incubated at a controlled temperature for an extended period of time. At predetermined time intervals, the wells of the test trays are individually examined for an indication of color change or other test criteria. However, this process can be long and tedious when performed manually by a technician. In addition, the incubation times for identification and susceptibility test trays may differ, or the optimal time to read a test result from the test tray may not be known in advance. Thus, a technician may typically need to read and record results for a specimen at several different times, sometimes far apart, which may cause assignment or correlation errors.

Automated systems are desirable in performing these tests to minimize the technician handling time, as well as to minimize the possibility of human error. In addition, automated systems may be preferred because they generally can obtain results more rapidly and accurately than manual methods. One known microbiological testing apparatus for the automatic incubation and reading of microbiological samples employs a plurality of test trays having a plurality of wells which contain the samples or agents to be tested. The trays are first placed in an incubator, and are then moved to an inspection station after a sufficient incubation period. A light source is disposed above the tray and a pair of video cameras are disposed below the tray at the inspection station. Each video camera takes a video image of an entire tray, and the video image signal of the entire tray is sent to an image processor to be analyzed.

The image processor requires uniform lighting over the entire inspection station. Consequently, the processor records the background light level of each pixel within an area of interest corresponding to each well of the tray to account for variability in the light source. The image processor processes the video image of the tray and determines the number of pixels for a particular well whose intensity exceeds a predetermined threshold for that area of interest. If the number of pixels exceeds a predetermined number, a positive result is assigned to that well. The image processor analyzes the binary partial results from the wells to determine the possible identity of the microorganisms. The binary partial results are compared to prerecorded patterns of results for each type of test tray to identify the sample in question.

A microbiological testing apparatus for detecting the presence of a fluorescence emitting reaction resulting from the interaction of a reacting agent and a sample for detection, susceptibility, and identification testing, is also known. In this apparatus, multiple trays having a plurality of test chambers are contained within a carousel. This carousel is rotated to move one of the trays close to a detection area. A positioning mechanism then radially moves that tray out of the carousel and into the detection area, and a high-energy light source is disposed proximate to the tray. The light source provides narrow-band light sufficient to produce an emission fluorescence from the reaction within the test chambers, which in turn is detected by a video mechanism disposed opposite to the light source and behind the positioned tray. The video mechanism produces an image based on the emission wavelength.

Another test system is known for identifying bacteria using signals based on the intensity of monochromatic light reflected from specimens placed in a culture plate having a plurality of cells. A rotary disk containing six interference filters is interposed between a lamp and a group of optical fibers. The light from the lamp passes through a particular interference filter to produce monochromatic light of a certain wavelength. The filtered monochromatic light is guided by the optical fibers to be incident on respective cells of the culture plate. The disk is rotated so that the six different wavelength monochromatic lights are caused to be incident on the cells sequentially. The light reflected from the specimens is guided by additional optical fibers to corresponding phototransistors. A signal is derived for each specimen based on the intensity of the reflected monochromatic light. These signals are then analyzed to determine the identity of the specimen by calculating the difference, or ratio, between the signals and comparing that result with a reference value.

Although the above-described systems may be somewhat useful, each system fails to fulfill all of the requirements of a fully automated microbiological testing system. In particular, the known systems are not capable of simultaneously performing both colorimetric-type and fluorometric-type testing on multiple-well test panels, which is needed to obtain more accurate test results. Further, these systems are generally not designed to continuously gather test data from a plurality of multiple-well test panels in a quick and reliable manner. Moreover, the automated processing of these systems is limited.

In addition, the known systems do not examine multiple indicators of growth of the samples, and then base the MIC calculations on these multiple growth indicators. The use of data from multiple growth indicators is desirable to provide increased accuracy and integrity of the results. Furthermore, the known systems fail to employ a method of screening questionable MIC results. In particular, the known systems do not evaluate the quality and reliability of the MIC results to provide a probability or confidence value which indicates the level of certainty at which the MIC results are deemed to be correct.

Accordingly, a need exists for a system and method for an improved system and method for analyzing biological samples to determine the susceptibility of the samples to antimicrobial materials, and to provide MIC values for the antimicrobial materials with respect to the various samples.

SUMMARY OF THE INVENTION

An object of the present invention is to provide a system and method for analyzing samples, such as biological samples, to accurately and effectively determine the susceptibility of the samples to antimicrobial materials.

Another object of the present invention is to provide a system and method which measures multiple indicators of growth of the biological samples, and then uses these measurements to determine the susceptibility of the samples to the various antimicrobial materials to provide MIC values for the respective samples and antimicrobial materials.

A further object of the invention is to provide a system and method evaluating the calculated MIC values for respective samples and antimicrobial materials to provide a probability or confidence value which indicates the level of certainty at which the MIC values are deemed to be correct.

A still further object of the present invention is to provide a system and method for optically reading a biological sample contained in sample wells of a sample test panel having various types and concentrations of antimicrobial materials therein and, based on these readings, measuring a plurality of growth indicators of the samples that the system and method uses to determine the respective minimum inhibitory concentrations (MICs) at which the respective antimicrobial materials will inhibit growth of the sample.

These and other objects of the present invention are substantially achieved by providing a system and method for analyzing a sample contained in at least one sample well by directing a plurality of analyzing light waves of different wavelengths, such as red, green and blue, onto the sample contained in the sample well, and detecting a respective resultant light wave emanating from the sample for each of the analyzing light waves being directed onto the sample. The system and method then provides a result value representative of each respective resultant light wave, and mathematically combines the result values to provide at least two growth indicator values, such as the redox state and turbidity of the sample, each of which represents a respective growth characteristic of the sample. The method and system can perform the directing, detecting and mathematical combining steps on the sample in the sample well at a plurality of time intervals, such that each of the mathematical combining steps performed provides a set of growth indicator values for each of the time intervals.

The method and system can perform the above steps on a plurality of the sample wells at a plurality of time intervals to obtain a respective set of growth indicator values for each of the respective sample wells at each of the time intervals. The method and system can then further mathematically combine certain of the growth indicator values in the respective sets of growth indicator values for each of the sample wells to provide a respective sample well characteristic value, such as an MIC value, for each of the respective sample wells. The method and system can then group the sample well characteristic values into a plurality of groups, and compare the sample well characteristic values to each other in each of the respective groups to determine in which sample wells in each of the groups sample growth is inhibited.

Another aspect of the present invention lies in providing a system and method for determining at least one minimum inhibitory concentration (MIC) value for a sample contained in a sample container that includes a plurality of sample wells, each of which containing a portion of the sample and a respective material adapted to affect growth of the sample. The system and method take a respective set of readings of each respective sample well at each of a plurality of intervals of time to provide a respective set of values for each respective sample well at each of said intervals. The readings are taken, for example, by detecting a plurality of light waves of different wavelengths, such as red, green and blue, from each of the sample wells at each of said intervals to provide the respective sets of values for each respective sample well at each of the intervals. Also, in each of the respective sets of values, one of the values represents a redox state of its respective sample well and the other value represents a turbidity value of its respective sample well.

For each of the sample wells, the system and method mathematically combine the respective sets of values to provide a respective well characteristic value for each of the sample wells. The system and method then group the sample well characteristic values into a plurality of groups representative of respective groups of the sample wells, and compare the sample well characteristic values to each other in each of the respective groups to determine a respective MIC value for each of the groups of sample wells.

BRIEF DESCRIPTION OF THE DRAWINGS

These and other objects, advantages and novel features of the invention will be more readily appreciated from the following detailed description when read in conjunction with the accompanying drawings, in which.

DETAILED DESCRIPTION OF THE PREFERRED EMBODIMENTS

Figure 1:
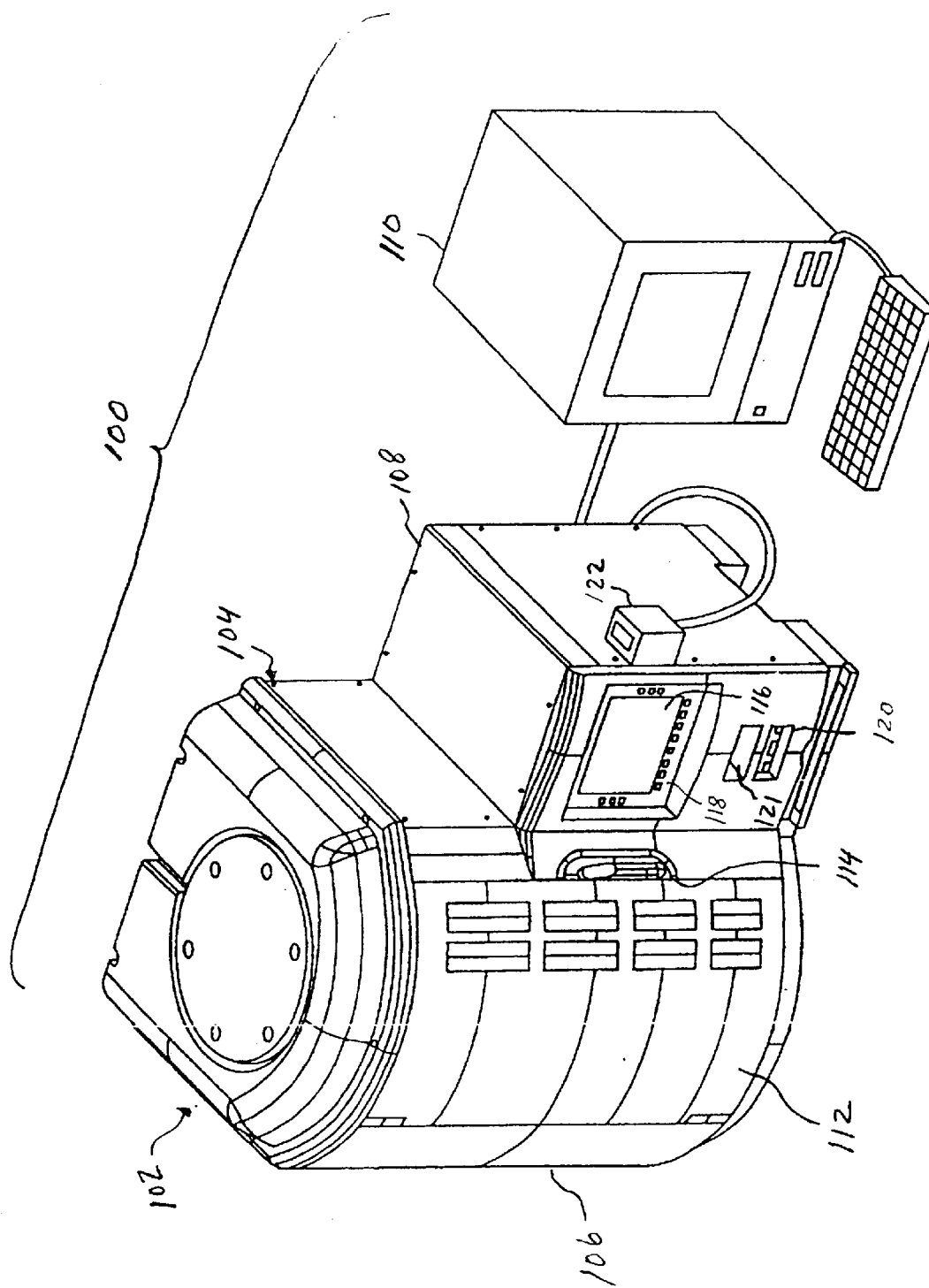
FIG. 1 illustrates a system for analyzing samples to determine their antimicrobial susceptibility according to an embodiment of the present invention.

FIG. 1 illustrates a system 100 according to an embodiment of the present invention for analyzing biological samples to identify the susceptibility of the samples to various types and concentrations of antimicrobial materials, and for calculating the minimum inhibitory concentration (MIC) at which the respective antibiotics or antimicrobial materials inhibit growth of the respective samples. The system 100 includes a measurement instrument 102 having an enclosure 104 which is divided into a carousel housing portion 106 and a controller housing portion 108. The system 100 further includes a workstation 110, such as a personal computer (PC) or the like, which is coupled to the controller housing portion 108 to communicate with the system 100 for purposes of transferring data to and from the system 100, for example.

The carousel housing portion 106 includes a door 112 and a latch mechanism 114. The latch mechanism 114 can maintain the door 112 in a closed state, and can be manipulated to allow the door 112 to be opened to expose an interior chamber 115 of the carousel housing portion 106. The controller housing portion 108 includes a display panel 116, a keyboard panel 118, a computer readable medium drive 120, and a barcode reader 122, the purposes of which are described in detail below.

Figure 2:
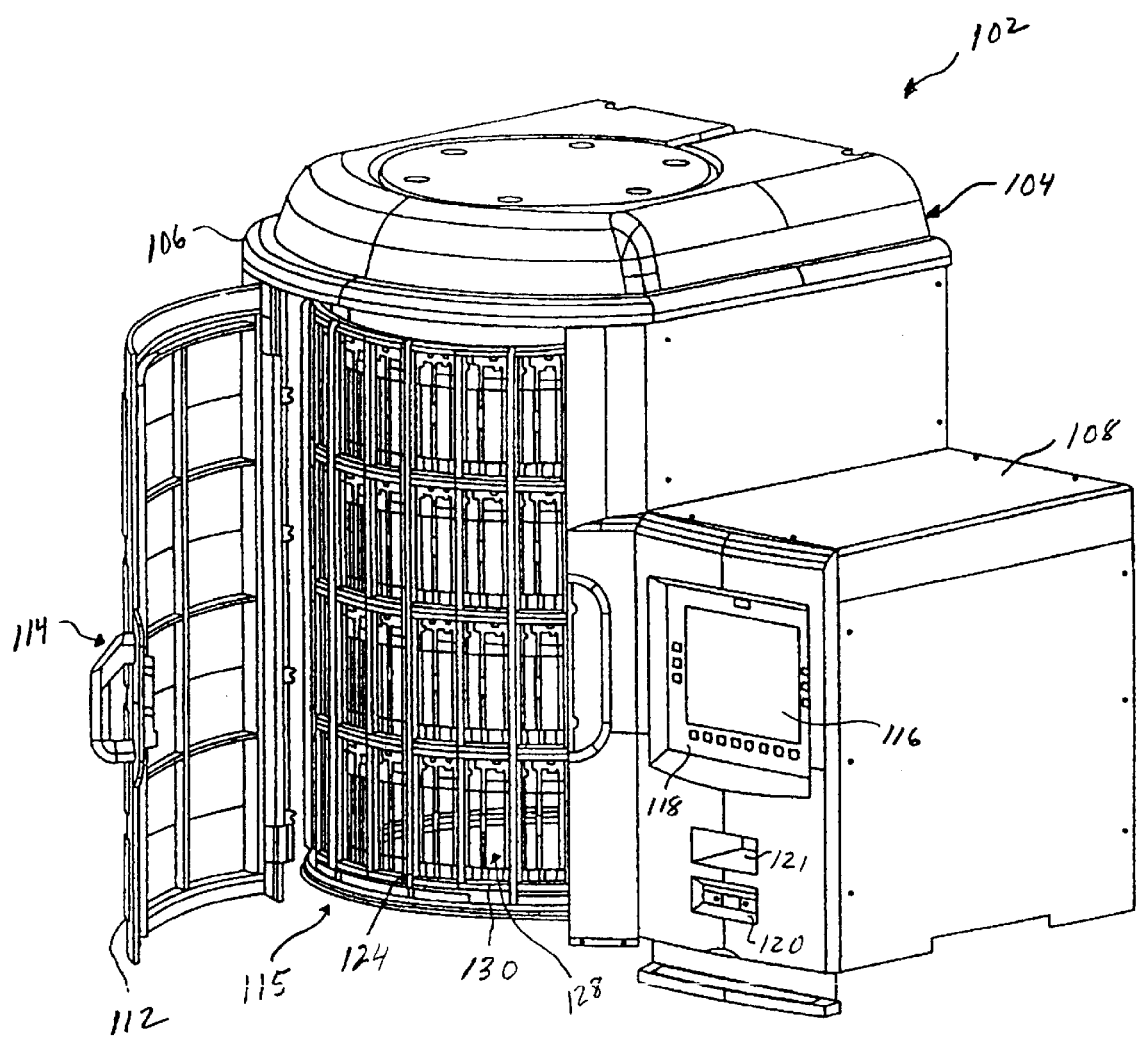
FIG. 2 illustrates a carousel housing portion of the system shown in FIG. 1.
Figure 3:
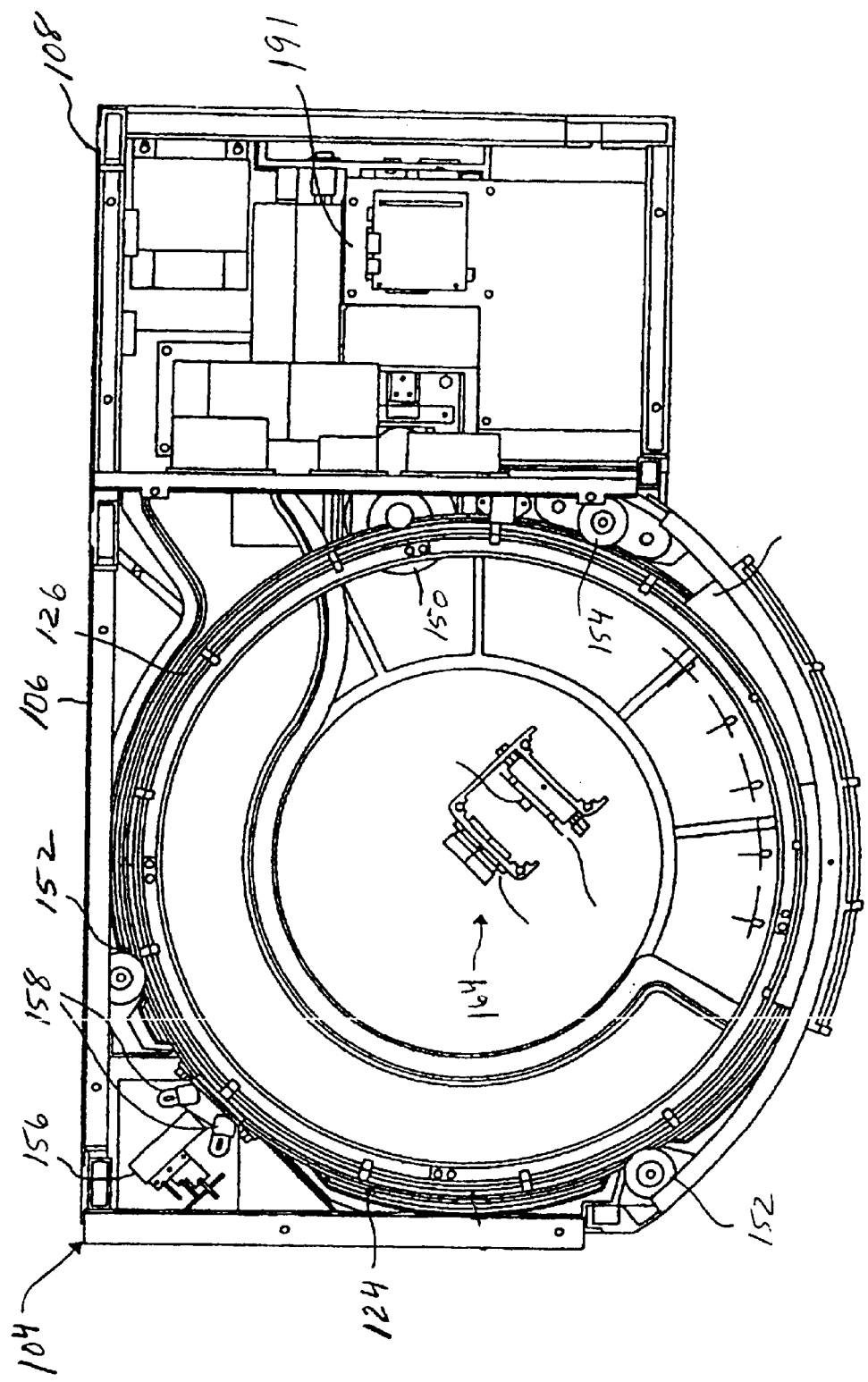
FIG. 3 is a top view of the carousel housing portion shown in FIG. 2 with the top of the enclosure removed.

As shown in FIGS. 2 and 3, a carousel 124 is housed in the interior chamber 115 of the carousel housing portion 106. The carousel 124 includes a plurality of rings and ribs bolted to a drive ring 126 to form a cylindrical cage, which is mounted vertically in the interior chamber 115. The carousel housing portion 106 is insulated to provide a substantially uniform temperature incubation environment in the interior chamber 115, and is light-tight under normal operation to prevent ambient light from entering the interior chamber 115, as described in more detail in copending U.S. patent application Ser. No. 09/083,130, referenced above.

In this example, the carousel 124 is arranged to include four horizontal tiers with each tier having twenty-six panel positions, thus providing a total of one-hundred and four panel positions 128. However, these numbers of tiers and panel positions 128 may be changed to accommodate the requirements of any specified application as will be appreciated by one skilled in the art. A panel carrier 130 is mounted in each of the panel positions 128. Each panel carrier 130 is configured to receive a test panel 132, an example of which is shown in FIGS. 4A–4C.

Figure 4A:
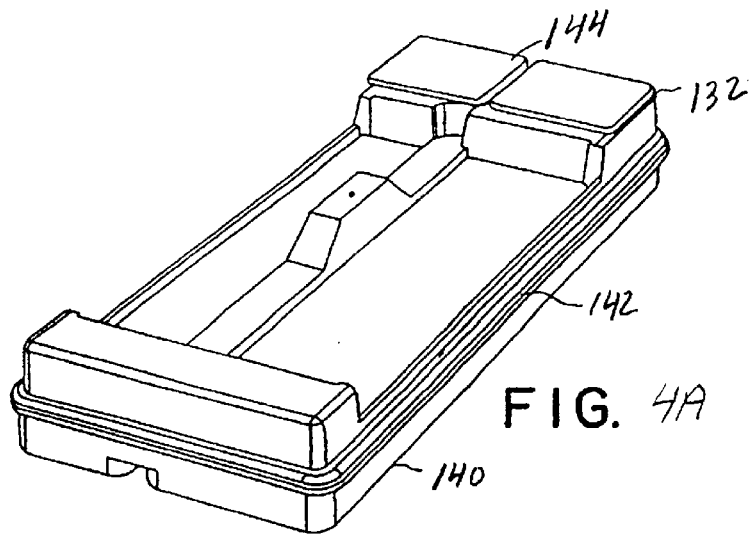
FIGS. 4A–4C are perspective, top and bottom views of an example of a test panel used in the system shown in FIG. 1.
Figure 4B:
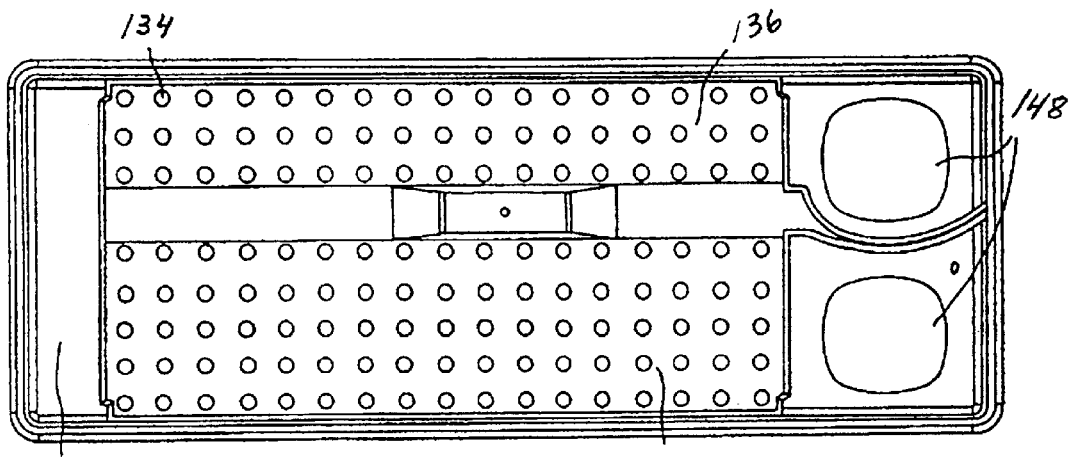
Figure 4C:
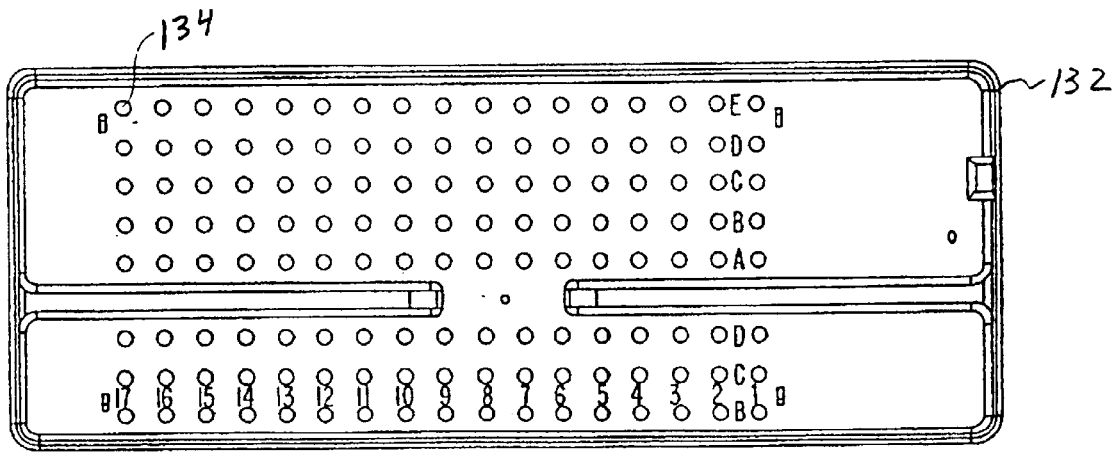

As shown in FIGS. 4A–4C, a test panel 132 is a disposable, transparent or semi-transparent device which is inoculated with materials or reagents needed for both identification (ID) and antimicrobial susceptibility determination (AST) testing of the samples. The testing is performed based on reactions that occur between the samples and reagents placed in individual wells 134 on each ID/AST test panel 132. The wells 134 are arranged on the ID/AST test panels 132 as a two-dimensional array having rows and columns. The wells 134 are segregated into a ID section 136 and an AST section 138. In this example, the ID section 136 includes fifty-one wells 134, and the AST section includes eighty-five wells 134. Each test panel 132 further includes a base 140, a chassis 142, a lid 144, a cellulose acetate pad 146, inoculation ports 148, and a panel label (not shown) which includes information that identifies the complete manufacturing history of that test panel 132. Further details of the test panels 132 used with the system 100 are described in copending U.S. patent application Ser. No. 09/083,130, referenced above, and in U.S. Pat. No. 5,922,593 to Livingston, the entire contents of which are incorporated herein by reference.

The panel carriers 130 are designed such that they will not retain improperly seated test panels 132. When the test panels 132 are mounted in the four tiers of the carousel 124, they are arranged to form substantially circular rows and vertical columns of wells 134. That is, all the columns of wells 134 in all four tiers of the carousel 124 should be substantially aligned with each other in the vertical direction along the entire height of the carousel 124, while all rows of wells 134 should be substantially aligned with each other around the entire circumference of the carousel 124. In this example, panel positions 128 are numbered zero through twenty-five in each tier of the carousel 124, with panel position zero being reserved for a normalization panel and thus not accessible by an operator during normal operation of the instrument 102.

The carousel housing portion 106 also includes a drive module 150 that drives the carousel 124 to rotate in a clockwise or counter-clockwise manner, as desired, and a plurality of bearings 152 and a spring-loaded pivot 154 which rotatably secure the carousel 124 in the interior chamber 115 of the carousel housing portion 106 and facilitate rotation of the carousel 124. Further details of the carousel 124 and its associated components, as well as the panel carriers 130 and test panels 132, are described in copending U.S. patent application Ser. No. 09/083,130, referenced above.

Figure 5:
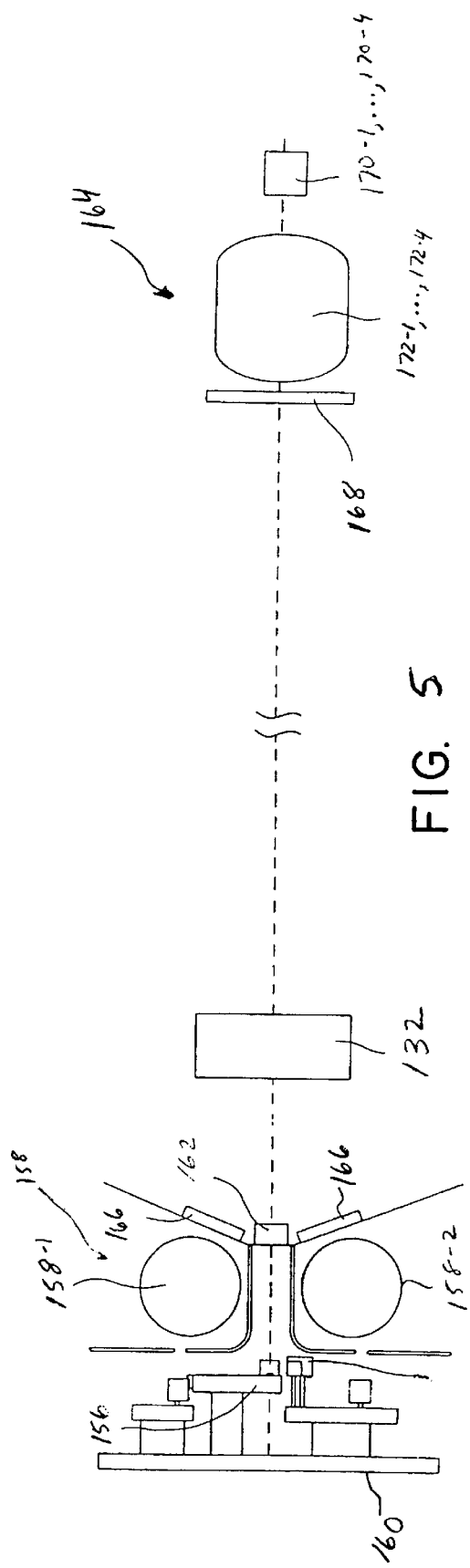
FIG. 5 is a diagrammatic view of the sample well reading components of the system shown in FIG. 1.
Figure 6:
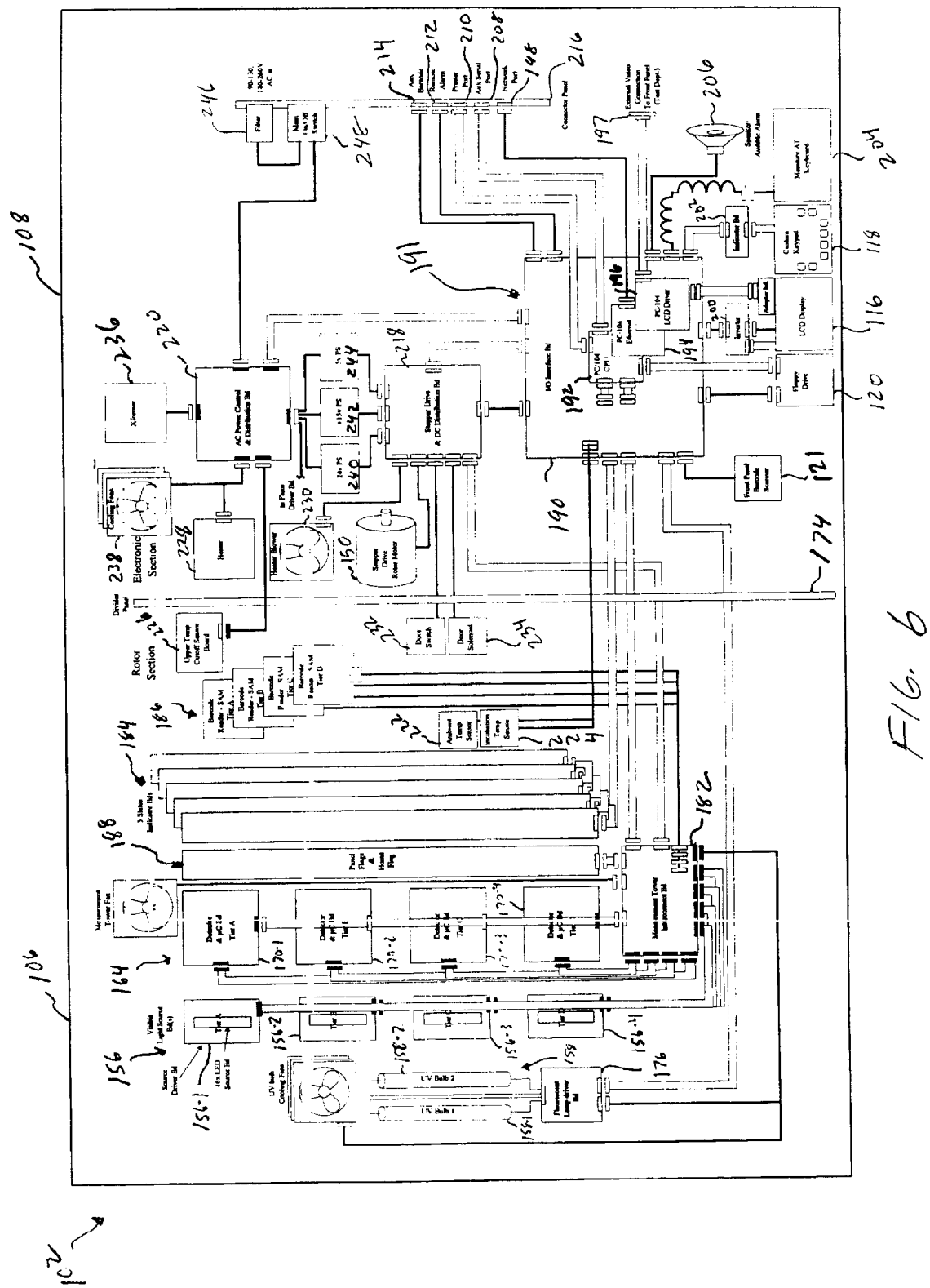
FIG. 6 is a schematic diagram illustrating the interrelationship among the mechanical and electrical components of the system shown in FIG. 1.

As shown in FIGS. 3 and 5, and in the schematic diagram shown of FIG. 6, the carousel housing portion 106 in this example further includes a visible light source assembly 156 and an ultraviolet (UV) light source assembly 158. The visible light source assembly 156 includes four visible light source modules 156-1 through 156-4 and a supporting tower 160, while the ultra-violet light source assembly 158 includes ultraviolet light sources 158-1 and 158-2. The supporting tower 160 aligns one visible light source module with each tier of the carousel 124 so that at any given time, one entire column of wells of the ID/AST test panels 132 in the four tiers of the carousel 124 can be illuminated by the visible light source modules.

In this example, each visible light source module 156-1 through 156-4 includes three parallel vertical columns of sixteen light-emitting diodes (LEDs) each. The first column consists of red LEDs, the second of green LEDs and the third of blue LEDs. A holographic diffuser plate 162 is disposed in close proximity to the ID/AST test panels 132 mounted in the carousel 124. The holographic diffuser plate 162 diffuses the illumination energy from each column of LEDs, when the columns are energized. Each column of LEDs is mounted in the visible light source modules to maintain a fixed distance from the diffuser plate 162. Cylindrical lenses (not shown) may be used to focus the illumination energy from each column of LEDs onto the vertical well columns of the ID/AST test panels 132. The illumination axis for each column of LEDs is made coincident for the red, green and blue illumination. Thus, each well column sees a uniform stripe of either red, green or blue illumination, depending upon which column of LEDs is energized.

As further shown in FIGS. 3, 5 and 6, an optical measurement system 164 is disposed approximately within the center of the carousel 124 such that it is aligned to receive the visible light transmitted through each well 134 of the ID/AST test panels 132 during excitation by red, green or blue illumination from the visible light source modules of the visible light source assembly 156. Visible fluorescent radiation is similarly detected from the wells 134 when the samples in the wells 134 are excited by the ultraviolet light emitted from the ultraviolet light source assembly 158. As can be appreciated by one skilled in the art, excitation filters 166 eliminate unwanted spectral components present in the light emitted from the ultraviolet light source assembly 158, and emission filters 168 eliminate unwanted spectral components that may be present in the output signal before detection by the optical measurement system 164.

In this example, the optical measurement system 164 includes a plurality of CCD detector modules 170-1 through 170-4 and corresponding lens assemblies 172-1 through 1724, with one CCD detector module 170 and one lens assembly 172 being aligned to receive readings from wells 134 of test panels 132 in a respective tier of the carousel 124. Accordingly, because the carousel 124 includes four tiers in this example, the optical measurement system 164 includes four CCD detector modules 170-1 through 170-4 and four corresponding lens assemblies 172-1 through 172-4, with each detector module/lens assembly pair arranged substantially in alignment in the vertical direction. The lens assemblies 172-1 through 172-4 focus light from of each panel well column of the test panels 132 in their respective tiers of the carousel 124 onto the CCD arrays of the corresponding CCD detector modules 170-1 through 170-4.

Each CCD detector module 170 can include, for example, a 2048-pixel linear CCD array. The CCD arrays of the CCD detector modules 170 detect and measure the intensity of light transmitted through each well 134 of the test panels 132 in the corresponding tiers of the carousel 124 when the wells 134 are illuminated by the red, green and blue LEDs. Visible fluorescent light is similarly detected by the CCD arrays of the CCD detector modules 170 when the samples in the wells 134 are excited by the ultraviolet light emitted from the ultraviolet light source assembly 158. Further details of the structure and operation of the visible light source assembly 156, ultraviolet light source assembly 158, optical measurement system 164, and their related components can be found in copending U.S. patent application Ser. No. 09/083, 130, referenced above.

As stated above, FIG. 6 is an exemplary schematic diagram illustrating further components of the measurement instrument 102 described above. As shown, the carousel housing portion 106 and the controller housing portion 108 are separated by a divider panel 174 which can be, for example, part of the housing 106. The ultraviolet light sources 158-1 and 158-2 are driven by a lamp driver 176. The lamp driver 176, visible light source modules 156-1 through 156-4, CCD detector modules 170-1 through 170-4, an ultraviolet light source cooling fan 178, and an optical measurement system cooling fan 180 are coupled to an interconnect board 182. A plurality of status indicator boards 184, barcode readers 186 which read the barcodes on the test panels 132, and panel flags and home flag reader 188, are also coupled to the interconnect board 182. Further details of the status indicator boards 184, barcode readers 186, and panel flags and home flag reader 188 can be found in copending U.S. patent application Ser. No. 09/083,130, referenced above.

The interconnect board 182 is coupled to an I/O interface board 190 of the controller module 191 that is present in the controller housing portion 108. As described in more detail below and in copending U.S. patent application Ser. No. 09/083,130, referenced above, the control module 191 includes a controller 192 which controls the visible light source modules 156-1 through 156-4, CCD detector modules 170-1 through 170-4, lamp driver 176, and all other components associated with performing the well reading process. The controller 191 further includes an ethernet 194 and an LCD driver 196. The ethernet 194 can be coupled to a network port 198 to output and input data to and from the workstation 110 (see FIG. 1), for example. The LCD driver 196 is coupled to the display) panel 116 (see FIG. 1) to display, for example, results of the well readings, and is further coupled to an external video connection 197. The controller 192 is coupled to the computer readable medium drive 120 (see FIG. 1) to output and input data to and from a computer readable disk, for example.

In addition, the controller module 191 is coupled to the computer readable medium drive 120, to the display panel 116 via an inverter 200, to the keyboard panel 118 via an indicator board 202, to the barcode reader 121, to an AT keyboard 204 and to a speaker 206. The controller module 191 is further coupled to an auxiliary serial port 208, a printer port 210, a remote alarm port 212 and an auxiliary barcode reader port 214 which, along with the network port 198, are housed in a connector panel 216. In this example, the barcode reader port 214 is coupled to the barcode reader 122 (see FIG. 1).

The controller module 191 is also coupled to a drive and DC distribution module 218 and a power control and distribution module 220. An ambient temperature sensor 222 and an incubation temperature sensor 224 sense the temperature inside the interior chamber 115 arid provide signals indicative of the temperature to the controller 192 of the controller module 191. Furthermore, upper temperature cut-off sensor 226 provides a signal to the controller 192 via the power control and distribution module 220 indicating when the temperature of the interior chamber 115 has reached the maximum temperature. In response, the controller 192 will control the heater 228 via power control and distribution module 220, and will control heater blower 230 via drive and distribution module 218, to prevent the temperature in the interior chamber 115 from further increasing. The controller 192 further controls the door switch 232 and door solenoid 234 via drive and distribution module 218 to control the latch mechanism 114 of the door 112 (see FIGS. 1 and 2) to either maintain the door 112 in the closed position or allow the door 112 to be opened. The controller 192 also controls the drive module 150 to control the rotation of carousel 124 as described in detail below. Further details of the temperature controlling operations and carousel rotation operations are set forth in copending U.S. patent application Ser. No. 09/083,130, referenced above.

As further shown in FIG. 6, the controller housing portion 108 includes a transformer 236 and cooling fans 248 that are coupled to the power control and distribution module 220. Also, a 24 V power supply 240, a 15 V power supply 242 and a 5 V power supply 244 provide power to the drive and distribution module 218 and power controller module 220, as well as to the lamp driver 176. These power supplies 240, 242 and 244 are powered from an A.C. input power that is received by the power control and distribution module 220 via filter 246 and the main on/off switch 248 of the system 100.

The operation of the system 100 will now be described with reference to FIGS. 1–6, as well as the flow chart and graphs shown in FIGS. 7A–9. In Step 1000, each test panel 132 is inoculated with a respective broth-suspended organism (i.e., a sample) before being placed into a respective panel carrier 130 of the carousel 124. The separate innocula are added manually to the inoculation ports 148 of the test panels 132, and allowed to flow into the wells 134 of the test panels 132 as described in copending U.S. patent application Ser. No. 09/083,130, referenced above. Only one type of sample is introduced into each respective test panel 132. As discussed above, the wells 134 of the test panels 132 include various types and concentrations of antimicrobial materials, which affect the growth of the samples, along with indicators that indicate the presence or absence of sample growth. Also, at least one of the wells 134 of each test panel 132 is designated as a growth control well and does not include any antimicrobial material.

The inoculated test panels 132 are then inserted into the respective panel carriers 130 of the carousel 124 in step 1010. The operator uses the barcode scanner 121 or barcode scanner 122 to scan the barcode of each test panel 132 as it is being inserted into a respective panel carrier 130, to thus enter information pertaining to the sample in the test panel 132, the antimicrobial materials in the test panel wells 134, and so on, into the system 100. The technician also can enter information pertaining to the tier level and position in the carousel 124 at which the test panel 132 is inserted via the keyboard 118, for example. Once the test panels 132 have been loaded into the carousel 124, the door 112 of the carousel housing portion 106 is closed and latched shut. In step 1020, the controller 192 controls the carousel 124 to begin rotating, and controls the heater 228 and heater blower 230 to begin increasing the temperature of the interior chamber 115 to incubate the samples in the wells 134. In this example, the operator can set the carousel 124 to rotate at one revolution per minute (RPM). However, the rotational speed can be set to any value as appropriate.

After a predetermined amount of time has passed, for example, two hours, the controller 192 controls the system 100 to begin taking measurements of the wells 134 of the test panels 132 in a manner as described in copending U.S. patent application Ser. No. 09/083,130, referenced above. In this example, measurements are taken at 20 minute intervals. Also, as can be appreciated from the discussion below, the following steps in the flowchart shown in FIG. 7 are performed for each panel 132, and the manner in which the processing proceeds for each respective panel 132 is dependent on the results of the well readings obtained for each respective panel 132. Also, the operations described in these steps are controlled by controller 192.

In step 1030, the first readings of the wells 134 of the test panels 132 are taken as test readings, to determine whether the readings pass an initial criteria indicating that the samples are valid for analysis. The well readings are taken as the carousel is being rotated. The controller 192 waits until the home flag of the carousel 124 is detected by the home flag detector 188 before beginning to take the readings, to insure that the controller 192 can match the readings with the correct well 134 from which the readings were taken.

The controller 192 can first control the detector modules 170-1 through 170-4 to perform dark readings, during which neither the UV light sources 158 nor the visible light sources 156-1 through 156-4 are energized. The controller 192 can then control the lamp driver 176 to drive the ultraviolet light source assembly 158. The controller 192 in this example waits until the carousel 124 has rotated two revolutions to allow the ultraviolet lights of the ultraviolet light source assembly 158 to warm up, so that the light intensity can stabilize, and then controls the detector modules 170-1 through 170-4 to take an ultraviolet light reading for an entire revolution of the carousel 124. The controller 192 then controls the lamp driver 176 to turn off the ultraviolet light sources 158, and processes the readings. As discussed in copending U.S. patent application Ser. No. 09/083,130 referenced above, the controller 192 uses the ultraviolet readings to identify the types of samples in the sample wells 134 of the test panels 132.

After the above readings have been taken, the visible light readings are then taken. The controller 192 can then control the rate of rotation of the carousel 124 to remain the same, or can increase the rate of rotation of the carousel 124, for example, to 2 RPM, or any other suitable rotation speed, while the visible light readings are being taken. In one example, the rotation speed is increased to 2 RPMs, and the red LEDs of the visible light source assembly 156 (see FIGS. 3, 5 and 6) are activated. The carousel 124 can be rotated one revolution to allow the red LEDs to warm up so that light intensity can stabilize, and then "red" readings can be taken of the wells 134 by the detector modules 170-1 through 1704 while the carousel 124 rotates the second revolution.

Once the red readings have been taken, the red LEDs are turned off and the green LEDs of the visible light 156 can be energized. As with the red LEDs, the carousel 124 can be rotated one revolution to allow the green LEDs to warm up to allow the light intensity to stabilize. The "green" readings can then be taken of the wells 124 by the detector modules 170-1 through 170-4 while the carousel 124 is rotated another revolution. After the green readings have been taken, the green LEDs are turned off. In this example, the rotation speed of the carousel 124 is then reduced to 1 RPM, and the blue LEDs of the visible light source assembly 156 are energized. The carousel 124 is allowed to rotate for one revolution while the blue LEDs warm up to allow the light intensity to stabilize. Then, the "blue" readings of the wells 134 are taken by the detector modules 170-1 through 110-4 during the next revolution of the carousel 124.

The red, green and blue readings taken for each well 134 of each test panel 132 are then stored by the controller 192 in a memory such that each well 134 has a specific red, green and blue reading for that particular time interval. The process then continues to step 1040 where the readings for each well 134 are evaluated to determine whether the further readings that are taken on a well 134 are to be considered valid.

In step 1040, the red readings taken of each well 134 are evaluated to determine whether the wells have been properly filled. The readings can range from an intensity level of "0" to an intensity level of "4200" with 0 being zero intensity and 4200 being the maximum intensity reading for a particular color (e.g., red). In this example, the process identifies in step 1040 the wells 134 having a red reading above 2200. For those wells 134 having such a red reading, the processing continues to step 1050 where those wells 134 are failed or, in other words, the system 100 identifies all future readings from those wells 134 as being invalid. Accordingly, either no further readings of those wells 134 are taken, or any readings that are taken are ignored.

Furthermore, if a well 134 has been identified as a growth control well and has a red reading of over 2200, the entire side of the test panel 132 on which that control well resides is failed. Also, if that well contains a particular antimicrobial material, no results are reported by the system 100 for that antimicrobial material for the particular test panels 132 including the failed wells.

Once the red well readings have been evaluated in step 1040 and the appropriate wells 134 have been failed in step 1050, the processing continues to step 1060 where a panel indicator determination is made. Specifically, in this step, the wells 134 identified as growth control wells for their respective test panels 132 are evaluated to determine whether the initial state of the growth indicator present in the samples in the control wells 134 of their respective test panels 132 are acceptable for evaluating those test panels 132. In this example, the value of the respective red reading for each control well is divided by the value of the respective green reading for each control well. If the result of the division is less than 0.3692 or greater than 0.6464, controller 192 determines that the initial state of the growth indicator is unacceptable for the test panel 132 including the control well providing this result. Accordingly, no results obtained by the well measurements for that particular test panel 132 are reported. As stated above, step 1060 is carried out for each test panel 132.

The processing then continues to step 1070 where the controller 192 will continue to rotate the carousel 124 and thus, the carousel housing portion 106 will continue to incubate the samples in the wells 134. The processing will continue to step 1080 where the system 100 will take the red, green and blue readings of the wells in a manner similar to that described to above with regard to step 1030, and as described in copending U.S. patent application Ser. No. 09/083,130, referenced above. The processing then proceeds to step 1090 where the controller 192 determines whether the minimum amount of incubation time has elapsed. The minimum incubation time at which readings of the wells 134 can begin to be analyzed to determine MIC values in this example is two hours. If the minimum incubation time has not elapsed, the processing returns to step 1070 and the incubation is continued. However, once the appropriate amount of incubation time has elapsed, the processing proceeds to step 1100 where the controller 192 will calculate the redox state and turbidity values for each well.

Figure 8:
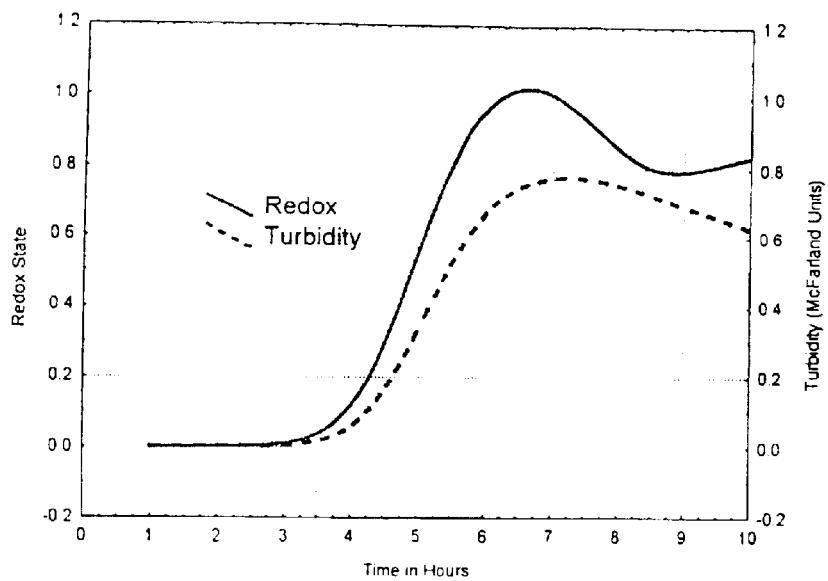
FIG. 8 is a graph illustrating redox states and turbidity values for a sample contained in one sample well of a test panel as calculated by the system shown in FIG. 1.

The system 100 in this example uses two indicators of growth, redox and turbidity, to evaluate the susceptibility of the samples to the antimicrobial materials in the wells 134. The redox and turbidity values are calculated for each well 134 in each of the panels based on the red, green and blue readings taken of the respective wells at the respective 20 minute time intervals as discussed above. A simultaneous nonlinear algorithmic model was developed from experimentally obtained redox and turbidity readings, and this algorithm is used by the controller 192 to predict the redox state and organism density (turbidity) in each of the wells 132. The controller 192 can arrange the calculated redox state and turbidity values for each respective well 132 in graph form with respect to incubation time. An example of the calculated redox and turbidity growth curves for *E.coli* for a single well 132 is shown in FIG. 8.

As stated above, the redox state of a sample in a well 132 is measured by utilizing the change in red, green and blue readings that occurs over time as a result of the reduction of a growth indicator, such as resazurin, by the antimicrobial material in the well 132. As the resazurin is reduced, the color of the sample in the well 132 changes from blue to red to clear. This change in redox is represented numerically as a continuum, with the value "0" indicating an unreduced growth indicator (blue=resazurin), the value "0.5" indicating that the indicator is 50% reduced (red=resorufin), and the value "1.0" indicating that the indicator has been completely reduced (clear=dihydroresorufin).

The turbidity is also estimated by using the red, green and blue reading in an equation similar to the redox calculation. The initial signal has a value of "0" and a maximum of 2.25 units can be estimated. The units for turbidity correspond to McFarland units (1 McFarland=$3\times10^8$ cfu/ml).

An example of the manner in which the actual red, green and blue readings are used to calculate redox and turbidity values will now be demonstrated. In this example, the red, green and blue readings taken of a sample well at the first twenty minute interval are as follows: red=873, green=956 and blue=2705. The processing then generates a one-column, four-row input matrix as shown in Table 1 as follows:

TABLE 1

| Input Matrix Values |
|---|
| 1.0000 |
| 2705.0000 |
| 0.3227 |
| 0.3534 |

It is noted that the first row in the input matrix is always padded with the value 1.0000. The value 2705.0000 is equal to the blue reading, the value 0.3227 is calculated by dividing the red reading by the blue reading (i.e., red/blue), and the value 0.3534 is calculated by dividing the green reading by the blue reading (i.e., green/blue). It is also noted that in this example, the blue reading is clamped at a starting value of 2705 until 36 minutes has elapsed in the incubation. All points after 36 minutes are multiplied by the value (2705/(blue signal @ last point before 36 minutes)). The result is then clamped to limits of 558 and 4474. Furthermore, the value of red/blue is clamped to a minimum of 0.2012329 and a maximum of 1.8936959, while the value of green/blue is clamped to a minimum of 0.3091655 and a maximum of 1.3084112.

The processing then multiplies the one-column, four-row Input Matrix by the four-column, five-row Redox Input Weight Matrix according to the equation "Input Matrix*Redox Input Weight Matrix" and known matrix multiplication techniques to arrive at a one-column, five-row matrix of numbers as discussed below. The twenty values in the Redox Input Weight Matrix have been calculated and programmed into the controller 192 based on past empirical data and observations, and remain constant for all of the readings at all of the time intervals. An example of the values of the Redox Input Weight Matrix are shown in the following Table 2:

TABLE 2

| Redox Input Weight Matrix Values | | | |
|---|---|---|---|
| −0.673253 | 0.000710423 | −1.623674164 | 3.340127166 |
| 2.445846 | −0.000572912 | 1.4797837 | −6.311909249 |
| 0.109425 | 0.005775254 | −3.604370752 | −0.242927922 |
| 1.356753 | 0.000748697 | −2.139010636 | −1.067568082 |
| 3.88E−05 | 0.022713989 | 3.80317E−05 | 2.99302E−05 |

The values of the Intermediate Matrix calculated according to the above equation "Input Matrix*Redox Input Weight Matrix" are shown in Table 3 as follows:

TABLE 3

| Intermediate Matrix Values |
|---|
| 1.9049 |
| −0.8571 |
| 14.4824 |
| 2.3143 |
| 61.4414 |

These values of the Intermediate Matrix, as well as the values of the Input Matrix, are used to create a one-column, nine-row Output Matrix. Specifically, the first row of the Output Matrix is padded with the value 1.0000, and rows two through six of the Output Matrix are calculated by taking the antilog value of each of the above values of the Input Matrix, respectively, according to the following equation:

$$\text{antilog value} = e^x/(1+e^x)$$

with x being the respective value from the matrix. Rows seven through nine of the Output Matrix are filled with the values in rows two through four of the Input Matrix. Accordingly, the values of the Output Matrix are shown in the following Table 4:

TABLE 4

| Output Matrix Values |
|---|
| 1.0000 |
| 0.8704 |
| 0.2980 |
| 1.0000 |
| 0.9101 |
| 1.0000 |
| 2705.0000 |
| 0.3227 |
| 0.3534 |

The redox value is then calculated by multiplying the one-column, nine-row Output Matrix by a nine-column, one-row Redox Output Weight Matrix according to the following equation and known matrix multiplication techniques.

$$\text{Redox Value} = \text{Output Matrix} * \text{Output Weight Matrix}$$

In this example, the values of the Redox Output Weight Matrix are shown in the following Table 5:

TABLE 5

| Redox Output Weight Matrix Values | | | | | | | | |
|---|---|---|---|---|---|---|---|---|
| −0.633973 | 4.167218646 | 1.721677475 | −0.389544272 | −2.543872 | −0.63391676 | 1.30610E−04 | 0.04646759 | −0.842252 |

As with the values of the Redox Input Weight Matrix, the Redox Output Weight Matrix values have been calculated and programmed into the controller 192 based on past empirical data and observations, and remain constant for all of the readings at all of the time intervals. The Redox Value is thus calculated as 0.23843516. This value is then plotted on the graph as shown in FIG. 8.

The turbidity value based on these red, green and blue readings is calculated in a similar manner. That is, the processing then generates a one-column, four-row input matrix as shown in Table 6 as follows:

TABLE 6

| Input Matrix Values |
|---|
| 1.0000 |
| 2705.0000 |
| 0.3227 |
| 0.3534 |

As with the Input Matrix Values for the redox calculation, the Input Matrix Values for the turbidity calculations are based on the actual red, green and blue readings. The first row in the input matrix is always padded with the value 1.0000. The value 2705.0000 is equal to the blue reading, the value 0.3227 is calculated by dividing the red reading by the blue reading (i.e., red/blue), and the value 0.3534 is calculated by dividing the green reading by the blue reading (i.e., green/blue). It is also noted that in this example, the blue reading is clamped at a starting value of 2705 until 36 minutes has elapsed in the incubation. All points after 36 minutes are multiplied by the value (2705/(blue signal @ last point before 36 minutes)). The result is then clamped to limits of 558 and 4474. Furthermore, the value of red/blue is clamped to a minimum of 0.2012329 and a maximum of 1.8936959, while the value of green/blue is clamped to a minimum of 0.3091655 and a maximum of 1.3084112.

The processing then multiplies the one-column, four-row Input Matrix by the four-column, five-row Turbidity Input Weight Matrix according to the equation "Input Matrix * Turbidity Input Weight Matrix" and known matrix multiplication techniques to arrive at a one-column, five-row matrix of numbers as discussed below. The twenty values in the Turbidity Input Weight Matrix have been calculated and programmed into the controller 192 based on past empirical data and observations, and remain constant for all of the readings at all of the time intervals. An example of the values of the Turbidity Input Weight Matrix are shown in the following Table 7:

TABLE 7

Turbidity Input Weight Matrix Values

| | | | |
|---|---|---|---|
| −2.870675 | 0.002111599 | −0.234543715 | 0.334025395 |
| −1.306260 | 0.00202755 | 0.577175204 | −2.717689223 |
| 3.477755 | 0.001837992 | −4.028539894 | 1.455268741 |
| −0.008775 | −0.004819911 | −0.027006746 | −0.01188475 |
| 8.842011 | 0.001408226 | −5.393142566 | −4.464335919 |

The values of the Intermediate Matrix calculated according to the above equation "Input Matrix*Turbidity Input Weight Matrix" are shown in Table 8 as follows:

TABLE 8

Intermediate Matrix Values 2.8836
3.4041
7.6637
−13.0596
9.3329

These values of the Intermediate Matrix, as well as the values of the Input Matrix, are used to create a one-column, nine-row Output Matrix. Specifically, the first row of the Output Matrix is padded with the value 1.0000, and rows two through six of the Output Matrix are calculated by taking the antilog value of each of the above values of the Input Matrix, respectively, according to the following equation:

antilog value=$e^x/(1+e^x)$ with x being the respective value from the matrix. Rows seven through nine of the Output Matrix are filled with the values in rows two through four of the Input Matrix. Accordingly, the values of the Output Matrix are shown in the following Table 9:

TABLE 9

Output Matrix Values 1.0000
0.9470
0.9678
0.9995
0.0000
0.9999
2705.0000
0.3227
0.3534

The turbidity value is then calculated by multiplying the one-column, nine-row Output Matrix by a nine-column, one-row Turbidity Output Weight Matrix according to the following equation and known matrix multiplication techniques.

Turbidity Value=Output Matrix*Output Weight Matrix

In this example, the values of the Turbidity Output Weight Matrix are shown in the following Table 10:

TABLE 10

Turbidity Output Weight Matrix Values

| | | | | | | | | |
|---|---|---|---|---|---|---|---|---|
| −0.107225 | −2.957877127 | 2.378329542 | 1.866207268 | 0.012793 | −1.741858375 | 1.38488E−04 | −0.08976299 | 0.401581 |

As with the values of the Turbidity Input Weight Matrix, the Turbidity Output weight Matrix values have been calculated and programmed into the controller 192 based on past empirical data and observations, and remain constant for all of the readings at all of the time intervals. The Turbidity Value is thus calculated as 0.00459741. This value is then plotted on the graph as shown in FIG. 8.

The redox and turbidity values are calculated for each well based on the readings taken for each well at each time interval (i.e., each twenty minute time interval in this example), and the values are plotted on a graph as shown in FIG. 8. A local regression algorithm (LOESS) smoothes the time series data for both the redox and turbidity values calculated for each well 132 over the elapsed period of time. The LOESS in this example uses no more than seven readings for each local regression. In evaluating a time point, at least one reading is required past the time point being interpolated. From the LOESS equations any reading at any time point can be estimated. From the interpolated data a series of metrics that describe the growth in the well are calculated. All metrics will be based on the time or growth control values derived from these smoothed and interpolated points. The metrics are derived from the basic functions such as absolute value, first derivative (rate), second derivative (acceleration) and integral (area under the curve). The metrics are then used to derive a series of variables that are utilized by the generalized additive models (GAMs) as described in more detail below. These variables are a variety of absolutes, maximums and ratios to the growth control. A total of 27 variables are available to the GAMs, as listed below in Table 11.

TABLE 11

Variables Available for GAMs

| Running Count | Abbreviation | Description |
| --- | --- | --- |
| 1 | CONC_LOG | drug concentration |
| 2 | T_AB | turbidity value |
| 3 | T_FD | turbidity first derivative |
| 4 | T_SD | turbidity second derivative |
| 5 | T_IN | turbidity integral |
| 6 | T_AB_M | turbidity maximum value |
| 7 | T_FD_M | turbidity maximum first derivative |
| 8 | T_SD_M | turbidity maximum second derivative |
| 9 | T_AB_M_R | turbidity maximum value/turbidity maximum value of the growth control |
| 10 | T_FD_M_R | turbidity maximum first derivative/turbidity maximum first derivative of the growth control |
| 11 | T_SD_M_R | turbidity maximum second derivative/turbidity maximum second derivative of the growth control |
| 12 | T_IN_R | turbidity integral/turbidity integral of the growth control |
| 13 | T_FD_T | time at turbidity maximum first derivative minus time at turbidity maximum first derivative of the growth control |
| 14 | T_SD_T | time at turbidity maximum second derivative minus time at turbidity maximum second derivative of the growth control |
| 15 | R_AB | redox value |
| 16 | R_FD | redox first derivative |
| 17 | R_SD | redox second derivative |
| 18 | R_IN | redox integral |
| 19 | R_AB_M | redox maximum value |
| 20 | R_FD_M | redox maximum first derivative |
| 21 | R_SD_M | redox maximum second derivative |
| 22 | R_AB_M_R | redox maximum value/redox maximum value of the growth control |
| 23 | R_FD_M_R | redox maximum first derivative/redox maximum first derivative of the growth control |
| 24 | R_SD_M_R | redox maximum second derivative/redox maximum second derivative of the growth control |
| 25 | R_IN_R | redox integral/redox integral of the growth control |
| 26 | R_FD_T | time at redox maximum first derivative minus time at redox maximum first derivative of the growth control |
| 27 | R_SD_T | time at redox maximum second derivative minus time at redox maximum second derivative of the growth control |

The processing then proceeds to step 1110 during which the calculated redox state for each growth control well in each respective test panel 132 is analyzed. If the maximum redox value for the growth control well of a test panel 132 is not above a desired value which, in this example, is 0.07, the processing continues to step 1120. In step 1120, the processing determines whether the elapsed incubation time has reached a certain desired duration which, in this example, is 16 hours. If the processing determines in step 1120 that 16 hours of incubation time or less has elapsed, the processing returns to step 1070 for this panel 132, and the process repeats as discussed above. However, if the processing determines in step 1110 that more than 16 hours of incubation time has elapsed for this particular panel 132, the processing proceeds to step 1130 where the panel 132 is failed as being inoculated or containing a non-reactive sample, and no test results are reported for that panel.

If the processing in step 1110 determines that the maximum redox state for the growth control well of the test panel 132 are greater than 0.07, the processing proceeds to step 1140 for that panel 132. In step 1140, the processing determines whether the maximum redox state for the growth control well of that panel 132 is greater than a predetermined value which, in this example, is 0.2. If the maximum redox state for the growth control well in that panel 132 is not greater than 0.2, the processing continues to step 1150 for that panel 132 where it is determined whether the elapsed incubation time is greater than a predetermined value which, in this example, is 16 hours. If the elapsed incubation time is less than or equal to 16 hours, the processing returns to step 1070 for this panel 132, and repeats as discussed above. However, if the processing determines in step 1150 that the elapsed incubation time has exceeded 16 hours, the processing continues to step 1160, where the test panel 132 is failed as having insufficient sample growth, and no results are reported for that test panel 132.

Concerning step 1140 discussed above, if the processing determines that the maximum redox state for the growth control well for the panel 132 is indeed greater than 0.2, the processing continues to step 1170 where the processing evaluates the type of curve represented by the calculated redox states plotted in graph form with respect to incubation time as shown, for example, in FIG. 8. Specifically, based on the maximum redox value of the growth control well of the panel 132, the processing determines whether the curve representing the redox values for the growth control well indicates that the sample is a slow or fast growing sample. If the processing determines in step 1170 that the curve is classified as a class "zero" curve, the sample is not yet classifiable as a slow or fast growing sample because a sufficient incubation time has not elapsed for that sample. Therefore, the processing returns to step 1070 for that panel 132, and repeats as discussed above. However, if the processing determines in step 1170 that the curve classification is other than "zero", the processing continues to step 1180.

probability would be 0.525. It is noted that five wells 134 of the test panel 132 contain different concentrations of this antimicrobial material, and the redox and turbidity results for each of these five wells is used by the GAM to determine the MIC.

TABLE 12

An Example of an MIC Calculation for Five Wells

| Antibiotic Concentration | 2 µg well | 4 µg well | 8 µg well | 16 µg well | 32 µg well |
|---|---|---|---|---|---|
| Pattern for MIC = 16 µg | Growth | Growth | Growth | No Growth | No Growth |
| Well Probability (p from the GAM) | 0.9 | 0.9 | 0.8 | 0.1 | 0.1 |
| Calculation | $p_2$ × | $p_4$ × | $p_8$ × | $1-p_{16}$ × | $1-p_{32}$ |

In step 1180, the processing determines whether the curve representing the redox states can be classified as a class "one" curve. If so, the processing continues to step 1190 where the controller 192 will perform the appropriate GAM on the redox states and turbidity values measured for each of the wells 134 in the test panel 132 to determine the MIC values for the particular sample and the anti-microbial materials contained in the wells 134 of the test panel 132.

In step 1200, the probability of sample growth for each well 134 of the test panel 134 is calculated according to the appropriate GAM once the growth control is above a specified threshold. The GAMs were developed for each antibiotic by evaluating a spectrum of species, MIC values and resistance mechanisms. The GAMs are specific for each antibiotic and broad category of organisms (gram positive/gram negative). Each GAM requires approximately 5 of the 27 variables previously described above in Table 11 to predict growth, but can use as many variables as deemed appropriate. A GAM uses a polynomial equation as shown below to describe the relationship between each variable included in the model and the contribution of that variable in predicting growth in a well. The calculation of the well probability $P_k$ is simply the sum of the polynomial functions for each variable and an intercept term.

$$\log\left(\frac{p}{p-1}\right) = \alpha + f_1(x_1) + \ldots + f_l(x_l)$$

Each polynomial function in the above equation represents the function associated with a respective variable chosen from Table 11. For example, $f_1(x_1)$ can represent the function for the first derivative of the turbidity curve at a particular time interval, $f_2(x_2)$ can represent the function for the second derivative of the turbidity curve at that time interval, and so on.

Figure 9:
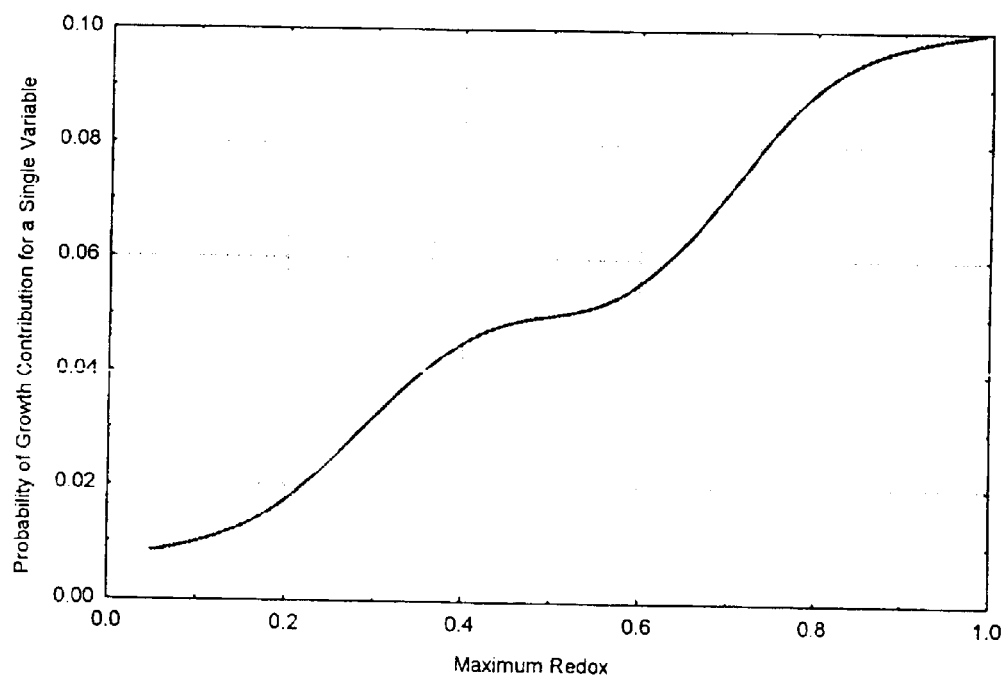
FIG. 9 is a graph illustrating the relationship between a variable and its indication of the probability of growth of a sample, which is evaluated by the system shown in FIG. 1 to derive an MIC value for the sample.

FIG. 9 illustrates a graph showing an example of the relationship between a variable and its prediction. These probabilities are then used to determine the MIC and calculate the confidence value for the reported MIC as follows.

Once a set of growth probabilities for each well 134 in the test panel 132 is derived by the GAM, a probability is calculated for every possible MIC in step 1210. This MIC probability is the product of the well probabilities with respect to the values obtained from the GAM. The example below shows the calculation for obtaining a probability for an MIC of 16 µg for one antimicrobial material with respect to the sample in the test panel 132. In this example, the raw After a raw probability is obtained, the processing proceeds to step 1220 where a confidence value for the most probable MIC is calculated. This is simply the raw probability (P) of the MIC value (k) over the sum of all valid MIC probabilities as shown in the following equation:

$$MIC \text{ Confidence Value} = \frac{P_k}{\sum_n P_k}$$

Once an MIC and the associated confidence value are calculated, processing proceeds to step 1230 where this information is evaluated with respect to a threshold. If the threshold is exceeded, then the processing proceeds to step 1240 where the system 100 reports the MIC for the particular sample in the test panel 132 with respect to the particular antimicrobial material in the group of wells 134 of the test panel 132. The system 100 can report the MIC on, for example, display screen 116 of FIGS. 1, 2 and 6, and can also control a printer (not shown) to generate a printed report.

However, if a low confidence value is obtained, the processing proceeds to step 1250 where it is determined whether the incubation protocol of a certain duration (e.g., 16 hours) has elapsed. If the incubation protocol has not elapsed, the processing returns to step 1070 where the test panel 132 continues to incubate and is reevaluated according to the processing discussed above after each 20 minute reading. On the other hand, if a minimum threshold is still not met at the end of the incubation protocol, the processing proceeds to step 1260 during which the system 100 does not report an MIC for that antimicrobial material, but rather, provides a message suggesting that the user check purity/viability and repeat the test.

Figure 10:
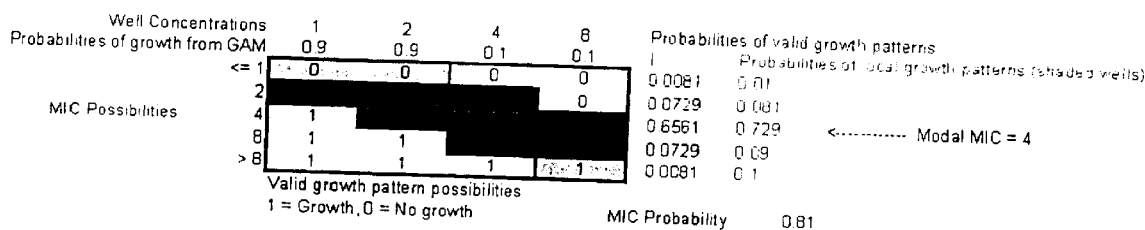
FIG. 10 is a table illustrating an example of MIC values and probabilities calculated according to an embodiment of the present invention.

A more detailed example of MIC probability calculations is shown in FIG. 10 for four wells having antibiotic concentrations of 1 µg, 2 µg, 4 µg and 8 µg, respectively. As illustrated in this example, the probability of growth for a well having a 1 µg concentration of antibiotic as calculated by the polynomial equation discussed above for a set of readings taken at a particular interval in time is 0.9. Also, the probabilities of growth for the wells having 2 µg, 4 µg and 8 µg are 0.9, 0.1 and 0.1, respectively. The five different growth possibilities are then entered into the table as shown, with the value "0" representing no growth and the value "1" representing growth. That is, as shown in the first row of the table, the condition in which no growth occurs (i.e., "0" for each well) is considered, meaning that the MIC value would be less than the minimum concentration of 1 µg. The second row illustrates the condition in which growth occurs in the 1 µg well but in no other wells, the third row illustrates the condition in which growth occurs in the 1 µg well and in the 2 µg well, but not in the higher concentration wells, and so on.

The four growth probabilities are then multiplied for each row to arrive at the probability of valid growth pattern values on the right side of the table. It is noted that because the probabilities of 0.9 or 0.1 at the top of the table represent probabilities of growth, these values are subtracted from 1 for conditions of non-growth to provide a value that is used in the multiplication. Considering the first row, for example, the probability of growth for the well concentration of 1 µg is "0.9". However, because no growth occurred in this well, the value used in the multiplication is "0.1" (i.e., 1−0.9). This is also the case for the 2 µg concentration well. Also, because the no growth occurred in the 4 µg and 8 µg wells, the values for these wells used in the multiplication are each "0.9" (i.e., 1−0.1). Accordingly, the multiplication values are 0.1*0.1*0.9*0.9=0.0081, which is the probability that this growth pattern in the first row is valid.

The above calculations are performed for each row to provide the values shown in the first column on right side of the table. In addition, the probabilities of the "local" growth patterns (i.e., the shaded wells in the graph) are multiplied to provide the probabilities of valid local growth patterns. This additional calculation is used to increase the accuracy of the results. As indicated, the row having the MIC possibility of "4" (the third row) provides the highest probabilities.

Using the MIC confidence value equation indicated above, the highest local growth pattern probability of 0.729 is divided by the sum of itself and the local growth pattern probabilities (i.e., 0.081+0.729+0.09) to arrive at a MIC probability of 0.81 as indicated. This value is then compared to a predetermined threshold. If the value exceeds the predetermined threshold, then the system can report the MIC value of "4" for this sample.

Figure 11:
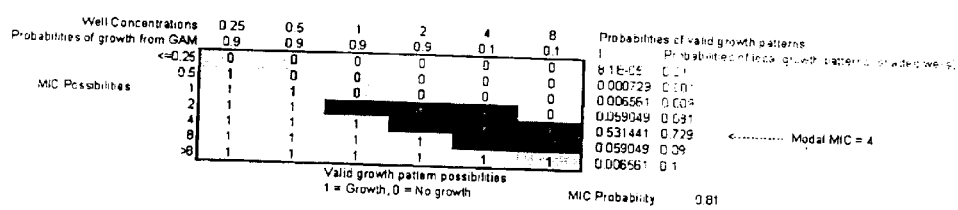
FIG. 11 is a table illustrating another example of MIC values and probabilities calculated according to an embodiment of the present invention.

An example of another table in which wells having antibiotic concentrations of 0.25 and 0.50 taken into account is shown in FIG. 11. The probabilities, MIC value and MIC probability are calculated in the same manner as described above.

Figure 7A:
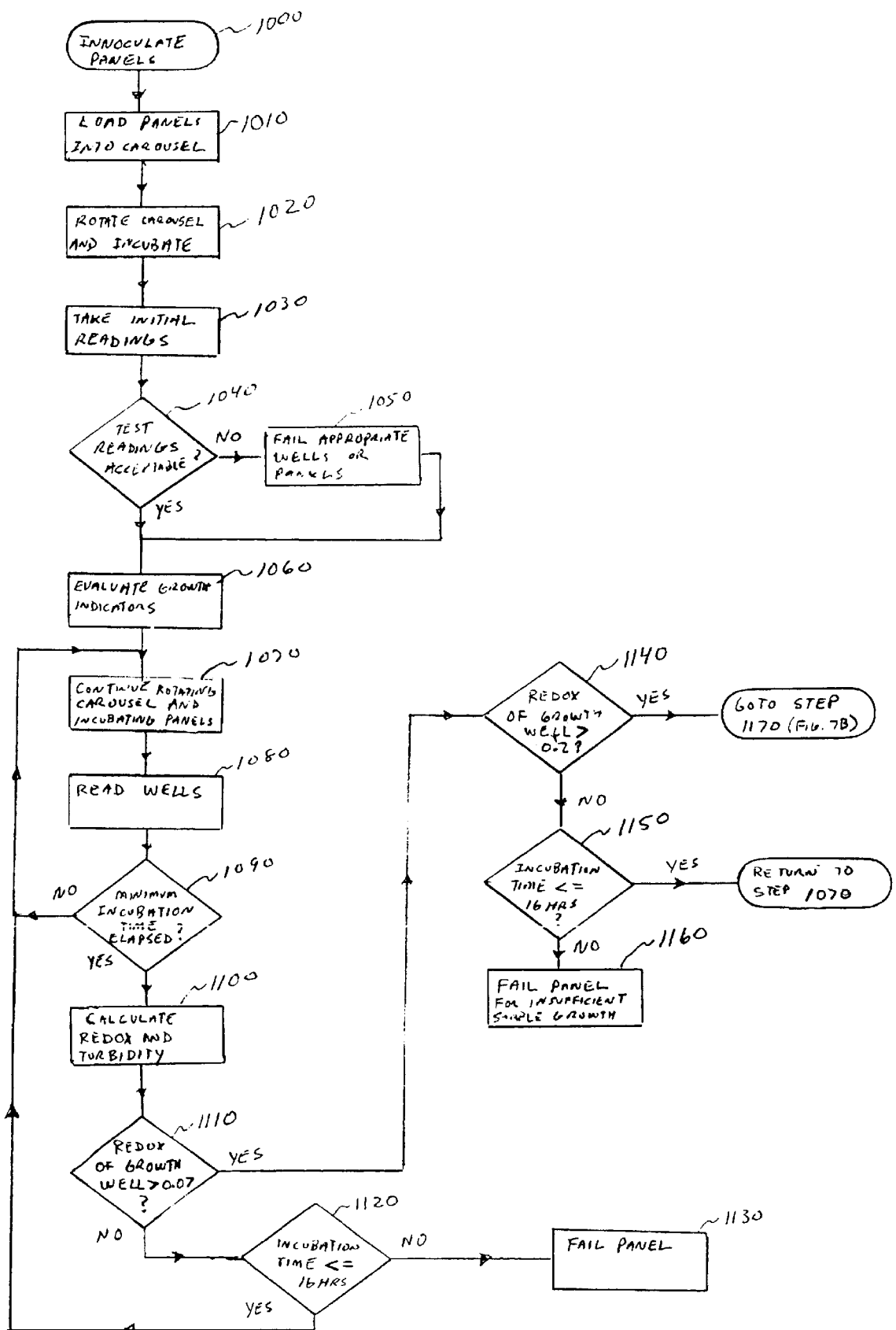
FIGS. 7A and 7B are flowcharts showing the steps performed by the system shown in FIG. 1 for analyzing samples contained in sample wells of the test panels as shown in FIGS. 4A–4C.
Figure 7B:
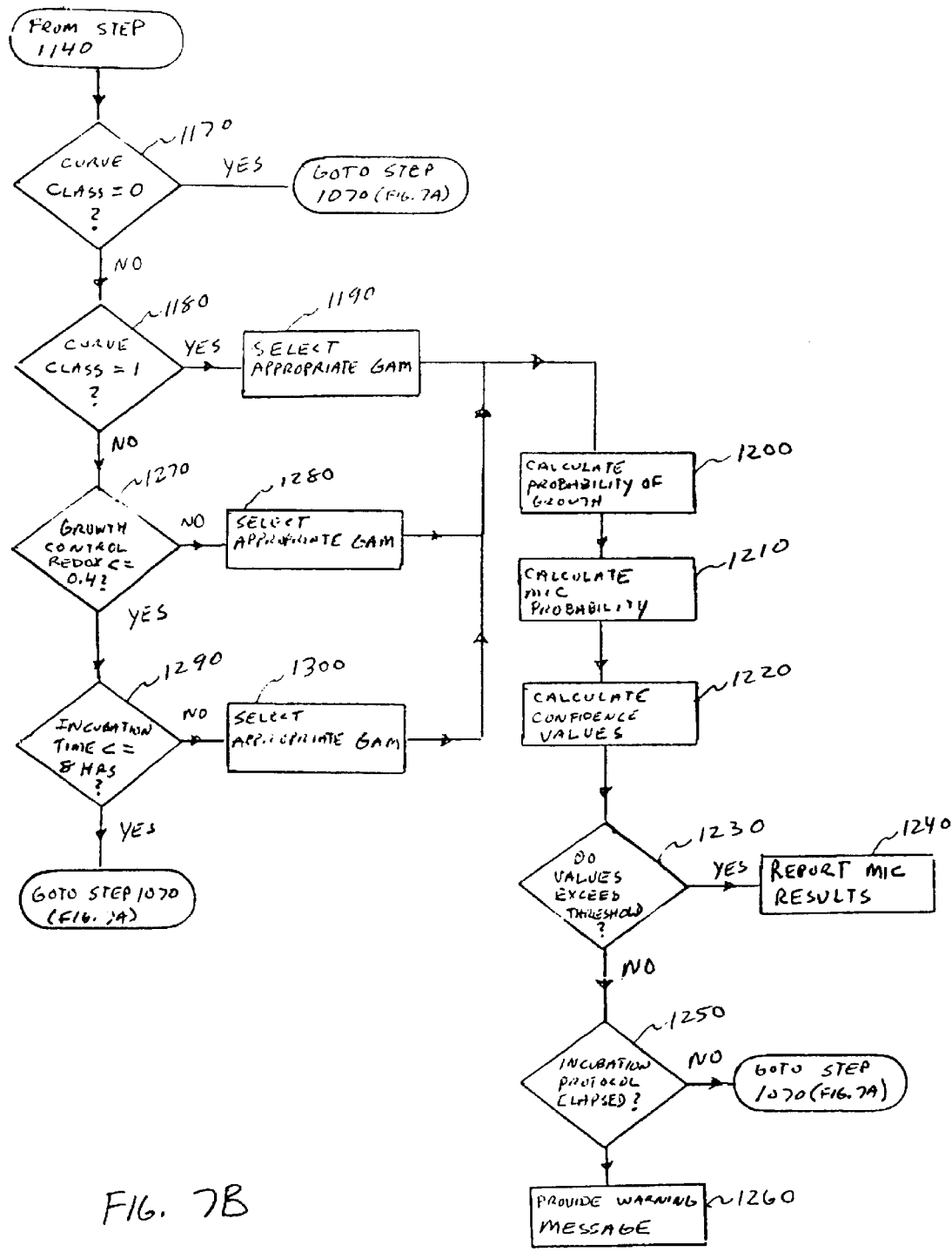
Figure 12:
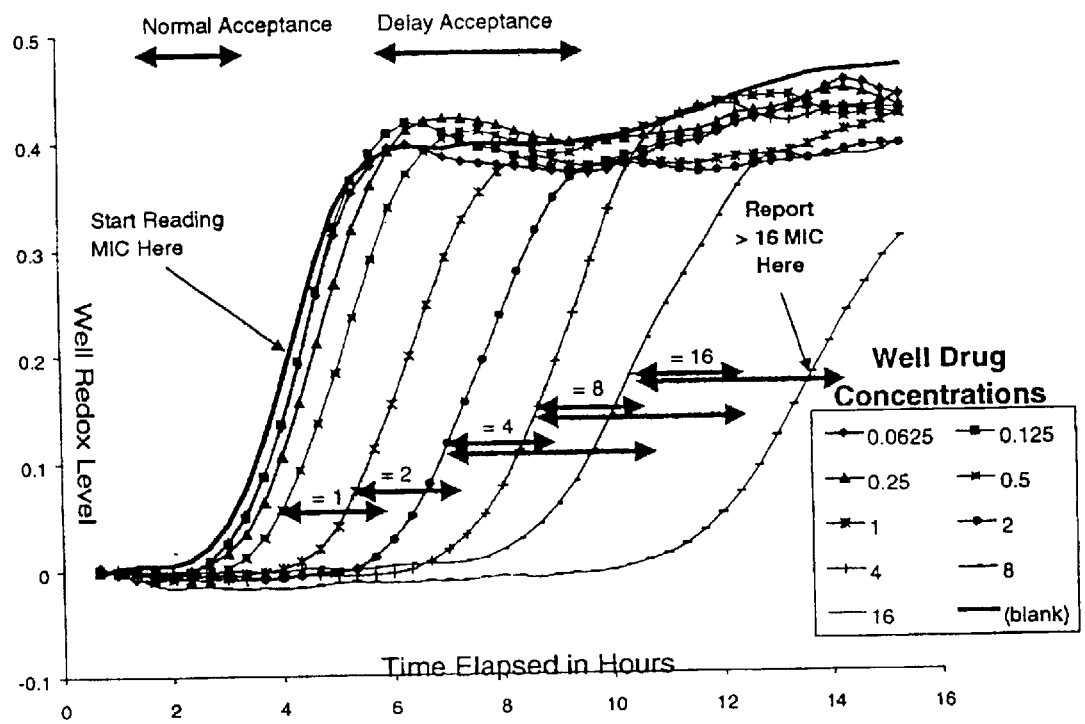
FIG. 12 is a graph illustrating the relationship between redox values for wells having different antibiotic concentrations in relation to elapsed incubation time.

It is also noted that prior to reporting the results in step 1240 shown in FIG. 7B, the processing can delay the reporting until the same MIC value has been determined for a desired number of consecutive, for example, three time intervals. That is, as can be appreciated from the graph of FIG. 12 showing redox values for wells having different antibiotic concentrations, the occurrence of growth in higher concentration wells can be delayed. For example, growth in a well having an antibiotic concentration of 1 µg can occur several hours after growth occurs in a well having an antibiotic concentration of 0.5 µg. Therefore, the accuracy of the results can be increased by refraining from reporting an MIC value until that value has been determined for a desired number of consecutive intervals, or a desired number of times within a certain number of consecutive intervals (e.g., 3 times out of 5 consecutive intervals). This delay reduces the possibility that a lower MIC value will be inadvertently reported.

It is noted that steps 1200 through 1260 of FIG. 7B are repeated as appropriate for each respective group of wells 134 containing a respective type of antimicrobial material, so that the MIC for each antimicrobial material in the test panel 132 can be reported for the sample.

Returning now to the discussion of step 1180 of FIG. 7B, if the processing in step 1180 determines that the curve representing the redox values for the wells 134 is not a class "one" curve, the processing proceeds to step 1270 where the processing determines whether the maximum redox state for the growth control well of the panel 132 is less than or equal to a particular value which, in this example is 0.4. If the maximum value of the redox state of the growth control well is not less than 0.4, it is determined that the sample is a slow growing sample. Accordingly, the processing continues to step 1280, where the controller 192 selects the appropriate GAM to be used to evaluate the redox and turbidity data for the wells 134 of the test panel. The processing then proceeds to step 1210 where the MIC values are determined as discussed above.

However, if the processing determines in step 1270 that the maximum redox state for the growth control well of the panel 132 is less than or equal to 0.4, the processing continues to step 1290 where the elapsed incubation time of the panel 132 is compared to predetermined value which, in this example, is 8 hours. If the elapsed incubation time is less than or equal to 8 hours, the processing returns to step 1070 and continues as discussed above. However, if the processing is greater than 8 hours, the processing continues to step 1300 where the controller 192 selects the appropriate GAM to be used to evaluate the redox and turbidity data for the wells 134 of the test panel. The processing then proceeds to step 1210 where the MIC values are determined as discussed above.

As mentioned previously, the processing discussed above is performed for each test panel 132 being rotated by the carousel 124 of FIGS. 2 and 3. Once all of the test panels 132 have been evaluated, and the MIC values relating to their respective samples have been reported, the controller 192 of Gi. 6 controls the heater 228 and heater blower 230 to discontinue heating the inner chamber 115. The controller 192 also controls the carousel 124 to stop rotating, and unlatches the door 112. The technician can then remove the test panels 132 and, if desired, commence a new series of tests using new test panels 132.

Although only one exemplary embodiment of the present invention has been described in detail above, those skilled in the art will readily appreciate that many modifications are possible in the exemplary embodiment without materially departing from the novel teachings and advantages of this invention. All such modifications are intended to be included within the scope of the invention as defined in the following claims.

What is claimed is:

1. A method for analyzing a microbiological sample contained in at least one sample well, comprising the steps of:

directing a plurality of different analyzing light wavelengths onto said microbiological sample contained in said sample well;

detecting a respective resultant light wavelength emanating from said microbiological sample for each of said analyzing light wavelengths directed onto said microbiological sample;

generating a result value representative of each respective resultant light wavelength; and mathematically combining said result values to provide at least two growth indicator values, each representing a respective growth characterisitic of said microbiological sample, wherein at least one of said growth indicator values represents a redox state of said microbiological sample, and wherein another of said growth indicator values represents a turbidity value of said microbiological sample.

2. A method as claimed in claim 1, wherein:

said directing step directs at least three of said analyzing light wavelengths onto said sample.

3. A method as claimed in claim 2, wherein:

said three analyzing light wavelengths include red, green and blue light wavelengths.

4. A method as claimed in claim 1, wherein:

said sample is contained in a plurality of said sample wells; and said directing, detecting and combining steps are performed for each of said sample wells.

5. A method as claimed in claim 1, wherein:

said directing, detecting and combining steps are each performed on said sample in said sample well at a plurality of time intervals, such that each of said combining steps provides a set of said growth indicator values for each of said time intervals.

6. A method as claimed in claim 1, wherein:

said sample is contained in a plurality of said sample wells; and said directing, detecting and combining steps are performed on said sample in each of said sample wells at each of a plurality of time intervals, such that each of said combining steps provides a respective set of said growth indicator values for each of said respective sample wells at each of said intervals.

7. A method as claimed in claim 6, further comprising the step of:

mathematically combining certain of said values in said respective sets of growth indicator values for each of said sample wells to provide a respective sample well characteristic value for each of said respective sample wells.

8. A method as claimed in claim 7, further comprising the step of:

grouping said sample well characteristic values into a plurality of groups; and comparing said sample well characteristic values to each other in each of said respective groups to determine in which sample wells in each of said groups sample growth is inhibited.

* * * * *